(12) United States Patent
Pan

(10) Patent No.: US 10,233,203 B2
(45) Date of Patent: Mar. 19, 2019

(54) PHOSPHAZENE COMPOUND, A PREPREG AND A COMPOSITE METAL LAMINATE

(71) Applicant: Guangdong Guangshan New Materials Co., Ltd., Guangdong (CN)

(72) Inventor: Qingchong Pan, Guangdong (CN)

(73) Assignee: GUANGDONG GUANGSHAN NEW MATERIALS CO., LTD., Guangdong (CN)

( * ) Notice: Subject to any disclaimer, the term of this patent is extended or adjusted under 35 U.S.C. 154(b) by 0 days.

(21) Appl. No.: 15/233,999

(22) Filed: Aug. 11, 2016

(65) Prior Publication Data

US 2017/0190725 A1 Jul. 6, 2017

(30) Foreign Application Priority Data

Jan. 4, 2016 (CN) .......................... 2016 1 0008253

(51) Int. Cl.
| | | |
|---|---|---|
| C07F 9/659 | (2006.01) | |
| C07F 9/6593 | (2006.01) | |
| C08K 5/5399 | (2006.01) | |
| C08J 5/24 | (2006.01) | |
| H05K 1/02 | (2006.01) | |
| H05K 1/03 | (2006.01) | |

(52) U.S. Cl.
CPC .......... *C07F 9/659* (2013.01); *C07F 9/65815* (2013.01); *C08J 5/24* (2013.01); *C08K 5/5399* (2013.01); *H05K 1/024* (2013.01); *H05K 1/0353* (2013.01); *C08J 2363/04* (2013.01); *C08J 2467/00* (2013.01); *C08J 2479/08* (2013.01); *C08L 2201/02* (2013.01)

(58) Field of Classification Search
CPC ...... C08J 5/24; C08J 2363/04; C08J 2467/00; C08J 2479/08; C07F 9/659; C07F 9/65815; C08K 5/5399; H05K 1/024; H05K 1/0353; C08L 2201/02
USPC ........................................................ 428/413
See application file for complete search history.

(56) References Cited

U.S. PATENT DOCUMENTS

| | | |
|---|---|---|
| 6,045,975 A | 4/2000 | Tani et al. |
| 6,403,755 B1 | 6/2002 | Stewart et al. |
| 2016/0244471 A1* | 8/2016 | He .................. C09K 21/12 |

FOREIGN PATENT DOCUMENTS

| | | |
|---|---|---|
| CN | 105153234 | 12/2015 |
| EP | 0443626 | 8/1991 |
| JP | 63241075 | 10/1988 |
| JP | H03246553 | 11/1991 |
| JP | H05286988 | 11/1993 |
| JP | H0782279 | 3/1995 |
| JP | H0782324 | 3/1995 |
| WO | 2012148194 | 11/2012 |
| WO | 2015188377 | 12/2015 |

OTHER PUBLICATIONS

Fantin et al., "Photosensitive Phosphazene Substrates: Synthesis and Characterization", Gazzetta Chimica Italiana, 1997, vol. 127, p. 287-292 (Year: 1997).*
Extended European Search Report for Application 16182167, dated Nov. 30, 2016, 9 pgs., European Patent Office, Germany.
Liu, X. et al., "Synthesis and Characterization of Brush-Shaped Hybrid Inorganic/Organic Polymers Based on Polyphosphazenes." American Chemical Society. 2012, pp. 1417-1426.

* cited by examiner

*Primary Examiner* — David T Karst
(74) *Attorney, Agent, or Firm* — McDonald Hopkins LLC

(57) ABSTRACT

The present invention relates to a phosphazene compound and a prepreg and a composite metal laminate. The phosphazene compound has a structure as shown in Formula (I). The present invention obtains a phosphazene compound using an M group having specific components. The composite metal laminates prepared by the epoxy resin composition comprising the phosphazene compound have low dielectric properties, good heat resistance and mechanical properties and is a low dielectric material also having great economic properties and being environmental friendly.

9 Claims, No Drawings

PHOSPHAZENE COMPOUND, A PREPREG AND A COMPOSITE METAL LAMINATE

BACKGROUND ART

For the purpose of safety, electronic products represented by mobile phones, computers, video cameras and electronic game machines, household and office electrical products represented by air conditioners, refrigerators, television images, audio products etc., and various products used in other areas require low dielectric properties and heat resistance.

In terms of electrical properties, the main factors needed to be considered also include the dielectric constant and dielectric loss of materials. Generally speaking, because the signal transmission speed of the substrate is inversely proportional to the square root of the dielectric constant of the substrate material, it is generally better that the dielectric constant of the substrate material is smaller; on the other hand, since the smaller dielectric loss presents the lower loss of signal transmission, the transmission quality provided by the material with smaller dielectric loss is better.

Therefore, a problem urgently to be solved in the field of printed circuit board materials at the present stage is how to develop materials with low dielectric constant and low dielectric loss and to apply them to the preparation of high frequency printed circuit boards.

CONTENTS OF THE INVENTION

In view of this, the first purpose of the present invention is to provide a phosphazene compound which has low dielectric properties, good heat resistance and mechanical properties and also has an advantage of low cost.

In order to achieve the above purpose, the present invention utilizes the following technical solution:

A phosphazene compound comprising a molecular structure as shown in Formula (I):

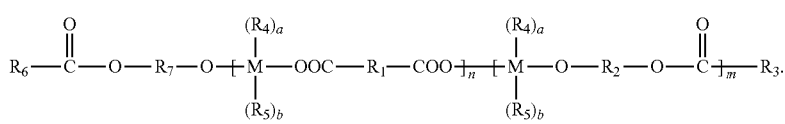

Formula (I)

In Formula (I), $R_1$ is substituted or unsubstituted aromatic hydrocarbon group or substituted or unsubstituted aliphatic hydrocarbon group; $R_2$, $R_3$, $R_6$ and $R_7$ are independently any organic group satisfying the chemical environment thereof; $R_4$ and $R_5$ are independently any inert nucleophilic group; M is any one of cyclotriphosphazene groups $M_1$, a cyclic ring consisting of four or more phosphazene groups $M_2$, or non-cyclic polyphosphazene groups $M_3$, or a combination of at least two of them; each n and m is an integer greater than or equal to zero, and n and m are not zero simultaneously; each a and b is an integer greater than or equal to zero, and a+b+2 equals to two times of the number of phosphorus atoms in M group.

Each n and m is an integer greater than zero, for example, 1, 2, 3, 4, 5, 6, 7, etc., and n and m are not zero simultaneously.

Each a and b is an integer greater than or equal to zero, for example, 0, 1, 2, 3, 4, 5, 6, 7, etc., and a+b+2 equals to two times of the number of phosphorus atoms in M group, namely ensuring the phosphorus atoms in M group is in a saturated state of pentavalent valence.

In the present invention, a and b represent the numbers of $R_4$ and $R_5$ groups which are connected to phosphorus atoms in M group.

In the present invention, said "satisfying the chemical environment thereof" means that the organic group can be connected to the adjacent atom to obtain a stable chemical bond.

Preferably, $R_1$ is any one of substituted or unsubstituted straight-chain alkylene, substituted or unsubstituted branched alkylene, substituted or unsubstituted cycloalkylene, substituted or unsubstituted arylene, substituted or unsubstituted heteroarylene, substituted or unsubstituted arylenealkylene, substituted or unsubstituted alkylenearylene, substituted or unsubstituted cycloalkylenearylene, substituted or unsubstituted heteroarylenealkylene or substituted or unsubstituted alkyleneheteroarylene.

Preferably, $R_2$ and $R_7$ are independently any one of substituted or unsubstituted straight-chain alkylene, substituted or unsubstituted branched alkylene, substituted or unsubstituted cycloalkylene, substituted or unsubstituted arylene, substituted or unsubstituted heteroarylene, substituted or unsubstituted arylenealkylene, substituted or unsubstituted alkylenearylene, substituted or unsubstituted cycloalkylenearylene or substituted or unsubstituted alkyleneheteroarylene.

Specifically, $R_1$, $R_2$ and $R_7$ are independently, but not limited to, any one of —$CH_2$—, —$CH_2CH_2$—, —$CH_2CH_2CH_2$—, —$CH_2CH_2CH_2CH_2$— or

Preferably, $R_3$ and $R_6$ are independently any one of substituted or unsubstituted straight-chain or branched alkyl, substituted or unsubstituted cycloalkyl, substituted or unsubstituted aryl, substituted or unsubstituted heteroaryl, substituted or unsubstituted aralkyl, substituted or unsubstituted heteroarylalkyl.

Preferably, $R_4$ and $R_5$ are independently any one of substituted or unsubstituted alkoxy, substituted or unsubstituted cycloalkoxy, substituted or unsubstituted aryloxy, substituted or unsubstituted arylalkoxy, substituted or unsubstituted alkylaryloxy, substituted or unsubstituted heteroarylalkoxy, substituted or unsubstituted alkylheteroaryloxy, substituted or unsubstituted carboxylate group, substituted or unsubstituted carbonate group, substituted or unsubstituted sulfonate group, substituted or unsubstituted phosphonate group, or a combination of at least two of them.

In the present invention, said "inert nucleophilic group" means a group which does not have active chemical reactivity and is not easy to react with other substances under conventional reaction conditions. The inert nucleophilic group can be used to cap carbon chain, and therefore is also known as capping group. For example, in the present invention, the inert nucleophilic group can be —$OCH_3$, -Ph (phenyl ring) or —$COOCH_3$, etc.

That provided in the present invention is a halogen-free phosphazene compound. Therefore, in the structure of Formula (I) in the present invention, all the groups and substituents of groups do not contain halogen.

In the present invention, nucleophile means those which can conduct nucleophilic substitution reaction with halogenated phosphazene. During the nucleophilic substitution reaction, nucleophile removes leaving groups, nucleophilic groups attack halogen atoms in halogenated phosphazene, and nucleophilic groups are attached to M. For example, when employing methanol $CH_3OH$ as a nucleophile to conduct nucleophilic substitution reaction with halogenated phosphazene, $CH_3OH$ removes $H^+$, nucleophilic group methoxyl $CH_3O$— substitutes the halogen atoms in halogenated phosphazene and is attached to —P in phosphazene.

In the present invention, the substituted or unsubstituted straight-chain or branched alkyl is preferably substituted or unsubstituted C1-C12 (for example, C1, C2, C3, C4, C5, C6, C7, C8, C9, C10 or C11) straight-chain or branched alkyl, further preferably C1-C8 straight-chain or branched alkyl. When the number of carbon atom is 1, it is methyl; when the number of carbon atom is 2, it is ethyl.

The substituted or unsubstituted cycloalkyl is preferably substituted or unsubstituted C3-C12 (for example, C4, C5, C6, C7, C8, C9, C10 or C11) cycloalkyl.

The substituted or unsubstituted alkoxy is preferably substituted or unsubstituted C1-C12 (for example, C2, C3, C4, C5, C6, C7, C8, C9, C10 or C11) alkoxy.

The substituted or unsubstituted cycloalkoxy is preferably substituted or unsubstituted C3-C12 (for example, C4, C5, C6, C7, C8, C9, C10 or C11) cycloalkoxy.

The substituted or unsubstituted aryl is preferably C7-C13 (for example, C8, C9, C10, C11 or C12) alkylaryl, preferably is phenyl, naphthyl,

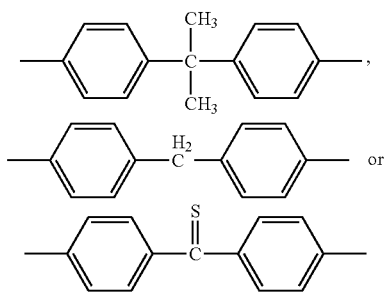

etc. Examples of phenyl include biphenylyl, terphenylyl, phenylmethyl, phenylethyl, or phenylpropyl, etc.

The substituted or unsubstituted heteroarylalkyl is preferably C7-C13 (for example, C8, C9, C10, C11 or C12) heteroarylalkyl, preferably is five-membered or six-membered heteroaryl, further preferably is substituted or unsubstituted furyl or pyridyl.

The substituted or unsubstituted aralkyl is preferably C7-C13 (for example, C8, C9, C10, C11 or C12) aralkyl.

The substituted or unsubstituted aryloxy is preferably C7-C13 (for example, C8, C9, C10, C11 or C12) aryloxy.

The substituted or unsubstituted arylalkoxy is preferably C7-C13 (for example, C8, C9, C10, C11 or C12) arylalkoxy.

The substituted or unsubstituted alkylaryloxy is preferably C7-C13 (for example, C8, C9, C10, C11 or C12) alkylaryloxy.

The substituted or unsubstituted heteroarylalkoxy is preferably C7-C13 (for example, C8, C9, C10, C11 or C12) heteroarylalkoxy.

The substituted or unsubstituted alkylheteroaryloxy is preferably C7-C13 (for example, C8, C9, C10, C11 or C12) alkylheteroaryloxy.

The substituted or unsubstituted straight-chain alkylene is preferably C1-C12 (for example, C2, C3, C4, C5, C6, C7, C8, C9, C10 or C11) straight-chain alkylene.

The substituted or unsubstituted branched alkylene is preferably C1-C12 (for example, C2, C3, C4, C5, C6, C7, C8, C9, C10 or C11) branched alkylene.

The substituted or unsubstituted arylene is preferably C6-C13 (for example, C7, C8, C9, C10, C11 or C12) arylene.

The substituted or unsubstituted heteroarylene is preferably C5-C13 (for example, C6, C7, C8, C9, C10, C11 or C12) heteroarylene.

The substituted or unsubstituted alkylenearylene is preferably C7-C13 (for example, C8, C9, C10, C11 or C12) alkylenearylene.

The substituted or unsubstituted arylenealkylene is preferably C7-C13 (for example, C8, C9, C10, C11 or C12) arylenealkylene.

The substituted or unsubstituted alkyleneheteroarylene is preferably C6-C13 (for example, C7, C8, C9, C10, C11 or C12) alkyleneheteroarylene.

The substituted or unsubstituted heteroarylenealkylene is preferably C6-C13 (for example, C7, C8, C9, C10, C11 or C12) heteroarylenealkylene.

The term "substituted" used in the present invention means any one or more hydrogen atoms on a specified atom is/are substituted by a substituent selected from a specified group, with a condition that the specified atom does not exceed the normal valence thereof and the substituting result is forming a stable compound. When the substituent is an oxo group or a ketone group (i.e. =O), two hydrogen atoms on a specified atom are substituted. A ketone substituent does not exist on aromatic ring. "A stable compound" means a compound which can be separated robustly enough to an effective purity from the reaction mixture and be prepared into an effective compound.

In the present invention, preferably, the structure of $M_1$ is:

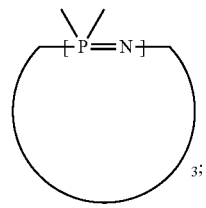

the structure of $M_2$ is:

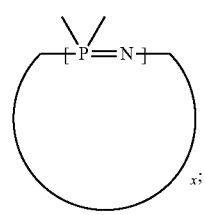

wherein, x is greater than or equal to 4;
the structure of $M_3$ is:

wherein, y is greater than or equal to 3.

It should be noted that, in the expression for structures of $M_1$ and $M_2$, the symbol of

is merely a schematic illustration for cyclic structure; in the structure

of the structural formulas of $M_1$, $M_2$ and $M_3$, the bonds connected to the P atom only represent that the substitutions of substituents take place on the P atom, and should not be construed as methyl.

Preferably, M represents a group of phosphorus nitrogen skeleton consisting of unsaturated phosphorous and nitrogen atoms, namely phosphazene group. Specifically, M contains at least 50 wt % of cyclotriphosphazene groups $M_1$, at most 48 wt % of $M_2$, which is a cyclic ring consisting of four or more phosphazene groups, and at most 48 wt % of non-cyclic polyphosphazene groups $M_3$.

In the present invention, the content of $M_1$ is at least 50 wt %, i.e. the content of $M_1$ can be 50-100 wt %. $M_1$ is a main component. When the content is 100 wt %, there is no $M_2$ and $M_3$. The typical but non-limited content of $M_1$ in the present invention can be 50 wt %, 51 wt %, 55 wt %, 58 wt %, 60 wt %, 65 wt %, 70 wt %, 74 wt %, 75 wt %, 80 wt %, 85 wt %, 90 wt %, 92 wt %, 95 wt %, 98 wt % or 100 wt %.

In the present invention, the content of $M_2$ is at most 30 wt %, i.e., the content of $M_2$ can be 0-30 wt %. When the content of $M_2$ is 0 wt %, it means that there is no $M_2$. The typical but non-limited content of $M_2$ in the present invention can be 0 wt %, 2 wt %, 5 wt %, 8 wt %, 11 wt %, 14 wt %, 16 wt %, 17 wt %, 19 wt %, 20 wt %, 22 wt %, 25 wt %, 27 wt %, 28 wt % or 29 wt %.

In the present invention, the content of $M_3$ is at most 45 wt %, i.e., the content of $M_2$ can be 0-45 wt %. When the content of $M_3$ is 0 wt %, it means that there is no $M_3$. The typical but non-limited content of $M_3$ in the present invention can be 0 wt %, 2 wt %, 5 wt %, 8 wt %, 10 wt %, 12 wt %, 14 wt %, 16 wt %, 18 wt %, 20 wt %, 23 wt %, 25 wt %, 27 wt %, 28 wt %, 30 wt %, 32 wt %, 35 wt %, 38 wt %, 40 wt %, 43 wt % or 45 wt %.

In the present invention, the sum of the mass percentages of $M_1$, $M_2$ and $M_3$ is 100%.

In the present invention, if the content of $M_1$ is less than 50 wt %, or the content of $M_2$ is more than 48 wt %, the reaction product of the compound and epoxy resin will have decreased heat resistance, humidity resistance and mechanical property in use. If the content of $M_3$ is more than 45 wt %, the reaction product of the compound and epoxy resin may result in inconvenient use due to large viscosity in use, and result in adverse consequence such as decreasing properties due to large molecular weight.

Preferably, the phosphazene compound is any one of the compounds having the following structures or a combination of at least two of them:

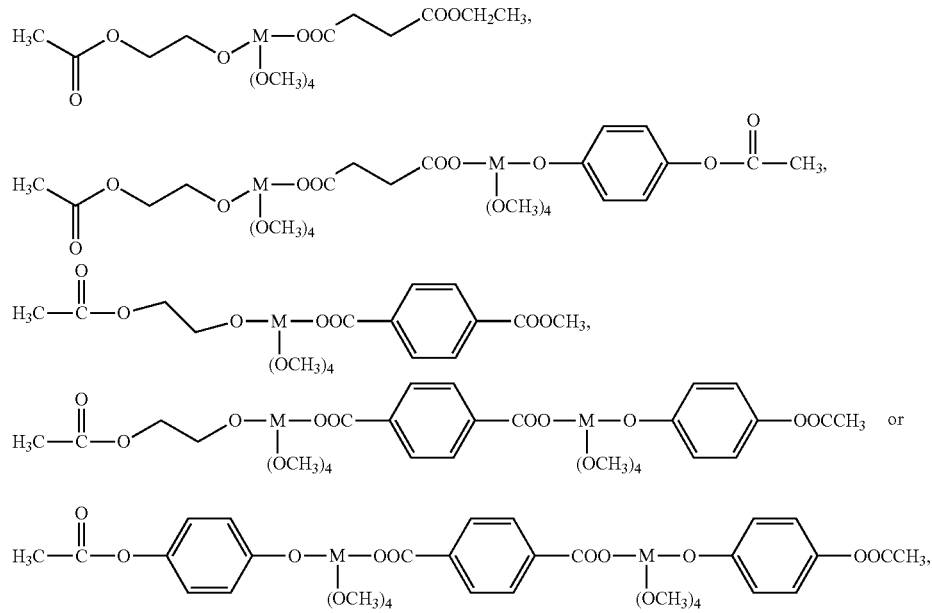

wherein M is a cyclotriphosphazene group.

In the Formula (I) of the present invention, capping groups of $R_3$, $R_4$, $R_5$ and $R_6$ can all be aromatic capping group. For example, $R_4$ and $R_5$ can be groups such as

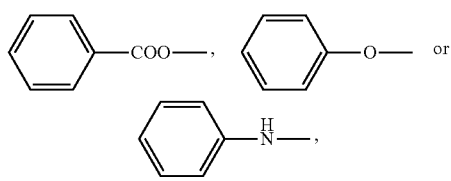

etc., and $R_3$ and $R_6$ can be phenyl, biphenylyl, benzyl, etc. For example, the compound of Formula (I) can be

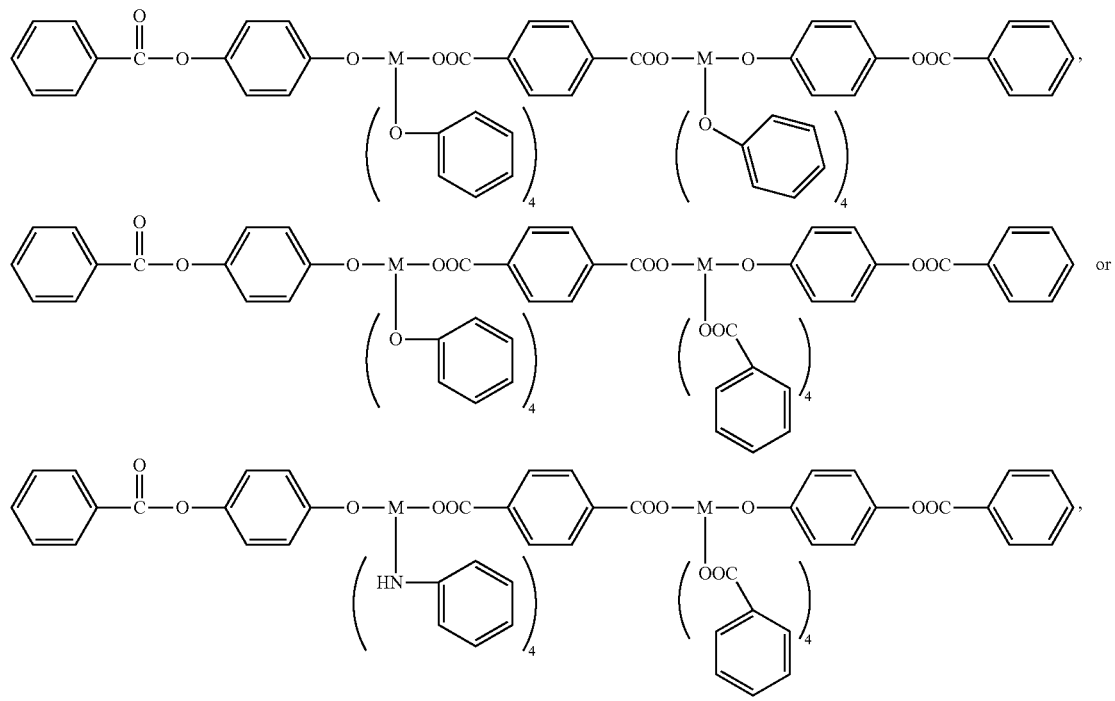

etc., wherein M is a cyclotriphosphazene group.

In another aspect, the present invention provides a method for preparing a phosphazene compound. The phosphazene compound prepared by this method has good heat resistance, good mechanical properties, and low dielectric constant.

A method for preparing the above phosphazene compound, obtains the phosphazene compound by carrying out a nucleophilic substitution reaction of phosphazene chloride and carboxylic acids and alcohols or phenols type nucleophile.

The phosphazene chloride refers to $M\text{-}Cl_{a+b+2}$, and the nucleophile refers to the nucleophile corresponding to the group connected to M group in Formula (I). For example, when $R_1$ is

the nucleophile which can carry out a nucleophilic substitution reaction with phosphazene chloride to make

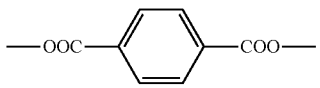

connect to phosphorus atoms of M is

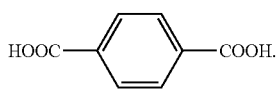

When $R_3$ is —$CH_2CH_2$—, the nucleophile which can carry out a nucleophilic substitution reaction with phosphazene chloride to make —O—$CH_2CH_2$—O— connect to phosphorus atoms of M can be $OHCH_2CH_2OH$. By using the same method, the connection of $R_2$, $R_5$, $R_6$, $R_7$ with phosphorus atoms of M can be achieved.

In the nucleophilic substitution reaction, chlorine atom in phosphazene compound is substituted. The nucleophilic substitution reaction can be carried out by methods well-known in the art. Specific examples of catalysts used in nucleophilic substitution reaction are metal chlorides such as zinc chloride, magnesium chloride, aluminum chloride; boron trifluoride and complexes thereof; Lewis bases such as sodium hydroxide. These catalysts may be used alone or in combination, which is not specifically defined in the present invention. The "phosphazene chloride" herein refers to a compound obtained by connecting the M group of Formula (I) to Cl. The phosphazene chloride can be prepared by using well-known solvents, catalysts according to a well-known reaction scheme, or by treating and purifying or directly without purifying a chlorinated phosphazene compound prepared by using phosphorus pentachloride and ammonium chloride according to a well-known method, wherein, for the reaction of $PCl_5+NH_4Cl\rightarrow 1/n(NPCl_2)n+4HCl$, the reaction products are mainly trimers $(PNCl_2)_3$ (namely hexachlorocyclotriphosphazene) and tetramers $(PNCl_2)_4$, and pure hexachlorocyclotriphosphazene can be obtained by slowly subliming the reaction products under vacuum at 60° C. Chlorinated phosphazene compounds with a structure of a cyclic ring consisting of four or more phosphazene groups and chlorinated non-cyclic polyphosphazene can also be prepared by known techniques.

In the reaction of nucleophile and phosphazene chloride, a nucleophile can be firstly used to react with phosphazene chloride to partly substitute chlorine atom(s) in the phosphazene chloride, and then, another nucleophile is used to react with the phosphazene chloride to obtain the phosphazene compound having the structure of Formula (I). In addition, a phosphazene compound comprising one or more M groups in its structure can be obtained by controlling the amount relationship between sub stances.

In another aspect, the present invention provides an epoxy resin composition having low dielectric properties, good heat resistance and good mechanical properties.

The epoxy resin composition comprises the phosphazene compound of the present invention.

Epoxy resin, curing agent and other fillers of the epoxy resin composition can utilize well-known epoxy resins, curing agents and fillers in the art.

The epoxy resin composition can also contain other polyesters in addition to the polyesters comprising phosphazene structure described previously.

In another aspect, the present invention provides a prepreg prepared by impregnating a substrate with the above epoxy resin composition or coating the above epoxy resin composition onto a substrate.

The substrate can be a glass fiber substrate, a polyester substrate, a polyimide substrate, a ceramic substrate or a carbon fiber substrate, etc.

Here, the specific process conditions of impregnation or coating are not particularly limited. The "prepreg" is a "bonding sheet" well-known by those skilled in the art.

A composite metal laminate comprising more than one sheet of the prepregs described above and prepared by coating a metal layer on the surface of the prepregs, overlapping and pressing successively.

Here, the material of the surface-coated metal layer is aluminum, copper, iron and alloys of any combination thereof.

Specific examples of the composite metal laminate are CEM-1 copper clad laminate, CEM-3 copper clad laminate, FR-4 copper clad laminate, FR-5 copper clad laminate, CEM-1 aluminum clad laminate, CEM-3 aluminum clad laminate, FR-4 aluminum clad laminate or FR-5 aluminum clad laminate.

A flexible copper-clad laminate, which comprises at least one prepreg as mentioned above and a copper foil overlaying at one side or both sides of the superimposed prepregs.

A wiring board prepared by processing wirings on the surface of the composite metal laminate as described above.

The raw materials of the epoxy resin composition form a coating having good low dielectric properties on the composite metal laminate by curing, and this can improve the wide use of the wiring board in industries of machine, equipment, instrument, meter, etc. which need wiring boards, for example electronic industry, electrical and electrical appliance industry, transportation industry, aerospace industry, toy industry, etc.

The above term "xxxyl or group" refers to the remaining parts of the molecular structure of corresponding compounds after one or more hydrogen atoms or other atoms or atomic groups are removed.

The present invention employs M groups of specific components to obtain a phosphazene compound, so as to make the cured products of the epoxy resin composition prepared from the phosphazene compound have low dielectric properties, good heat resistance and mechanical properties and be a low dielectric material also having great economic properties and being environmental friendly. The copper-clad laminate prepared from the flame retardant compound has a dielectric constant (1 GHz) of 3.28-3.33, a dielectric loss (1 GHz) of 0.005-0.006, a Tg which can be 175° C. or greater, a T-peeling strength which can be 1.90 kg/mm$^2$ or greater, an interlaminar peeling strength which can be 1.64 kg/mm$^2$ or greater, and a saturated water absorption which can be 0.35% or less.

EMBODIMENTS

The technical solutions of the present invention are further explained by combining with the following examples.

In the following examples, the used raw material of phosphazene chloride (for example hexachlorocyclotriphosphazene) can be obtained by the synthetic methods described in the present invention or known in the art. The other raw materials can be obtained through commercial purchase.

Example 1

The phosphazene compound of the present example has the following structure:

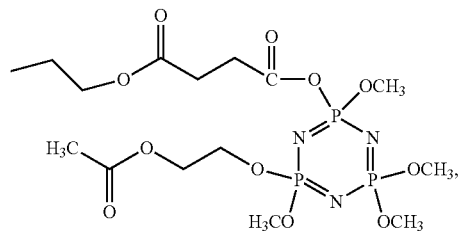 [SMILES: CCCOC(=O)CCC(=O)OP1(OC)=NP(OC)(OCCOC(C)=O)=NP(OC)(OC)=N1]

and the preparation method thereof is shown as follows.

1 mol of hexachlorocyclotriphosphazene, 200 ml of acetone, 4 mol of sodium methylate, 1 mol of ethylene glycol were added to a 3-neck glass reactor having a volume of 2000 ml and having a stirring apparatus. While stirring, nitrogen was fed therein, and the reactor was heated to 60° C. 620 g of 20% sodium hydroxide solution was dripped within 60 min, and then the mixture was held at 60° C., stirred and reacted for 8 hours. After reaction, the inorganic constituents and water in the system were removed by physical method. Then 3 mL of 98% concentrated sulfuric acid was dripped and 1 mol of butanedioic acid was added therein, and the mixture was stirred and reacted for 5 hours, followed by adding 1 mol of ethanol and continuing to stir and make the mixture react for 2 hours. After reaction, the impurities and water in the system were removed by physical methods; and the solvent in the system was distilled off to obtain 1 mol of ester compound A having an ester equivalent of 180 g/eq and a structure as shown above.

The obtained compound A was characterized by nuclear magnetic resonance hydrogen spectrum, and the results are as follows:

$^1$H NMR (CDCl$_3$, 500 MHz): δ 4.15-4.22 (m, 4H, COOC$\underline{H}_2$), 3.83 (m, 2H, COOC$\underline{H}_2$C$\underline{H}_2$O), 3.42 (s, 12H, OCH$_3$), 2.58-2.60 (m, 4H, COC$\underline{H}_2$C$\underline{H}_2$CO), 2.1 (m, 3H, COC$\underline{H}_3$), 1.63 (m, 2H, CH$_3$C$\underline{H}_2$O), 1.0 (m, 3H, C$\underline{H}_3$CH$_2$O).

Characteristic peak positions in infrared spectroscopy: ester carbonyl, 1730-1740 cm$^{-1}$; C—O—C in ester group, 1200 cm$^{-1}$; characteristic absorption peak of P=N bond in the skeleton of phosphazene, 1217 cm$^{-1}$; P—N in the skeleton of phosphazene, 874 cm$^{-1}$; absorption peak of methyl ether, 2995.3 cm$^{-1}$; absorption peak of P—O—C bond, 1035 cm$^{-1}$; absorption peak of CH$_2$—O, 2983 cm$^{-1}$.

90 g of the above ester compound A as a curing agent was added into 100 g of o-cresol novolac epoxy resin with an epoxide equivalent of 200 g/eq and 0.2 g of curing accelerator 2-methylimidazole to prepare an epoxy resin composition. A standard copper clad laminate sample meeting the national, UL and other standards was prepared by using this epoxy resin composition according to generally used copper clad laminate production process. The copper clad laminate is named as copper clad laminate a and the properties thereof are measured and the results are shown in Table 1.

Example 2

The phosphazene compound of the present example has the following structure:

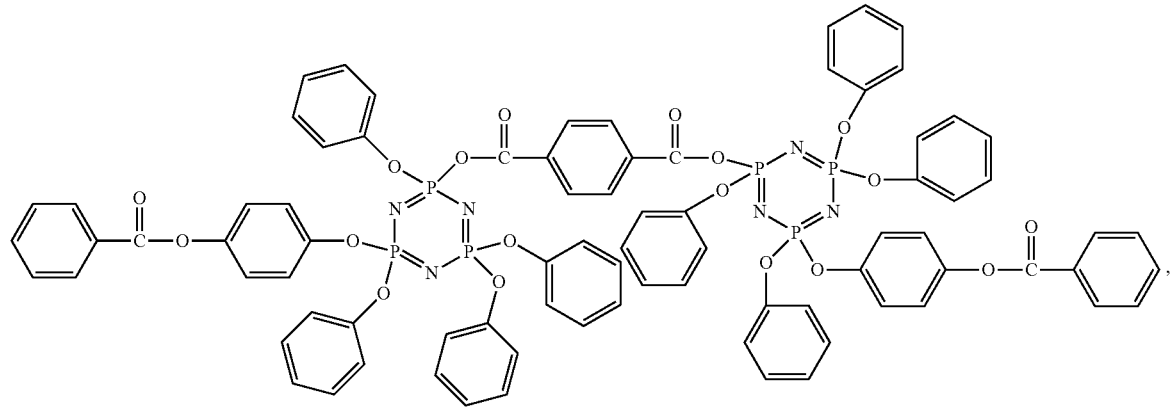 [SMILES: O=C(Oc1ccc(OP2(Oc3ccccc3)=NP(Oc3ccccc3)(Oc3ccccc3)=NP(OC(=O)c3ccc(C(=O)OP4(Oc5ccccc5)=NP(Oc5ccccc5)(Oc5ccc(OC(=O)c6ccccc6)cc5)=NP(Oc5ccccc5)(Oc5ccccc5)=N4)cc3)(Oc3ccccc3)=N2)cc1)c1ccccc1]

and the preparation method thereof is shown as follows.

1 mol of hydroquinone, 1 mol of benzoic acid, 200 ml of acetone were added to a 3-neck glass reactor having a volume of 2000 ml and having a stirring apparatus. 3 mL of 98% concentrated sulfuric acid was dripped therein and the mixture conducted esterification reaction for 1 h, followed by adding 1 mol of hexachlorocyclotriphosphazene and 4 mol of phenol and stirring. While stirring, nitrogen was fed therein, and the reactor was heated to 60° C. 621 g of 20% sodium hydroxide solution was dripped within 60 min, and then the mixture was held at 60° C., stirred and reacted for 10 hours. After reaction, the inorganic constituents and water in the system were removed by physical method. Then 3 mL of 98% concentrated sulfuric acid was dripped and 1 mol of terephthalic acid was added therein, and the mixture was continued to react for 3 hours, followed by adding 1 mol of hexachlorocyclotriphosphazene and continuing to react for 5 hours, and then adding 4 mol of phenol and 1 mol of hydroquinone and continuing to react for 8 hours. After reaction, the impurities and water in the system were removed by physical methods; and the solvent in the system was distilled off to obtain 1 mol of ester compound B having an ester equivalent of 410 g/eq and a structure as shown above.

The obtained compound B was characterized by nuclear magnetic resonance hydrogen spectrum, and the results are as follows:

$^1$H NMR (CDCl$_3$, 500 MHz): δ 8.28-8.32 (m, 4H,

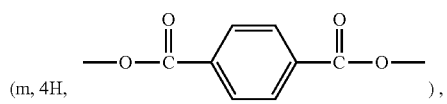

), 7.4-8.1 (m, 10H,

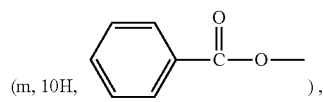

), 6.8-7.0 (S, 48H, hydrogen in

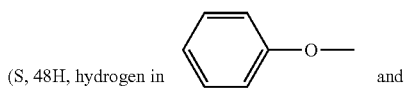 and

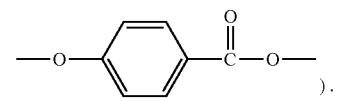

).

Characteristic peak positions in infrared spectroscopy: ester carbonyl, 1730-1740 cm$^{-1}$; C—O—C in ester group, 1200 cm$^{-1}$; characteristic absorption peak of P=N bond in the skeleton of phosphazene, 1217 cm$^{-1}$; P—N in the skeleton of phosphazene, 874 cm$^{-1}$; absorption peak of P—O—C bond, 1035 cm$^{-1}$; para-position substituted benzene ring, 860-790 cm$^{-1}$.

205 g of the above ester compound B as a curing agent was added into 100 g of o-cresol novolac epoxy resin with an epoxide equivalent of 200 g/eq and 0.2 g of curing accelerator 2MI to prepare an epoxy resin composition. A standard copper clad laminate sample meeting the national, UL and other standards was prepared by using this epoxy resin composition according to generally used copper clad laminate production process. The copper clad laminate is named as copper clad laminate b and the properties thereof are measured and the results are shown in Table 1.

Example 3

The phosphazene compound of the present example has the following structure:

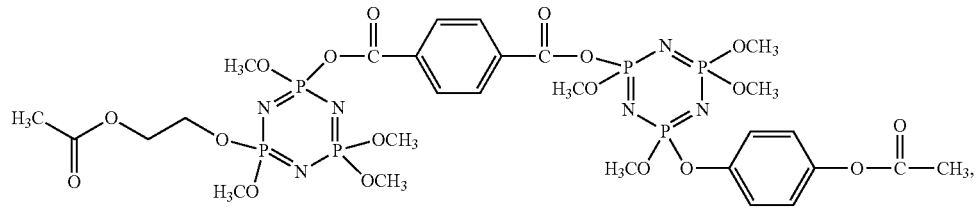 [SMILES: COP1(OC)=NP(OC)(OC(=O)c2ccc(C(=O)OP3(OC)=NP(OC)(Oc4ccc(OC(C)=O)cc4)=NP(OC)(OC)=N3)cc2)=NP(OC)(OCCOC(C)=O)=N1]

and the preparation method thereof is shown as follows.

1 mol of ethylene glycol, 1 mol of acetic acid, 200 ml of acetone were added to a 3-neck glass reactor having a volume of 2000 ml and having a stirring apparatus. 3 mL of 98% concentrated sulfuric acid was dripped therein and the mixture conducted esterification reaction for 1 h, followed by adding 1 mol of hexachlorocyclotriphosphazene and 4 mol of sodium methylate and stirring. While stirring, nitrogen was fed therein, and the reactor was heated to 60° C. 620 g of 20% sodium hydroxide solution was dripped within 60 min, and then the mixture was held at 60° C., stirred and reacted for 15 hours. After reaction, the inorganic constituents and water in the system were removed by physical methods. Then 3 mL of 98% concentrated sulfuric acid was dripped and 1 mol of terephthalic acid was added therein, and the mixture was continued to be held at 60° C. and react for 3 hours, followed by adding 1 mol of hexachlorocyclotriphosphazene and continuing to react for 3 hours, and then adding 4 mol of sodium methylate and continuing to react for 5 hours, and then dripping 1 mol of hydroquinone and continuing to react for 4 hours. After reaction, the inorganic constituents and water in the system were removed by physical methods. Then 3 mL of 98% concentrated sulfuric acid was dripped and 1 mol of acetic acid was added therein, and the mixture reacted for 3 hours. After reaction, the impurities and water in the system were removed by physical methods; and the solvent in the system was distilled off to obtain 1 mol of ester compound C having an ester equivalent of 225 g/eq and a structure as shown above.

The obtained compound C was characterized by nuclear magnetic resonance hydrogen spectrum, and the results are as follows:

$^1$H NMR (CDCl$_3$, 500 MHz): δ 8.28-8.32 (m, 4H,

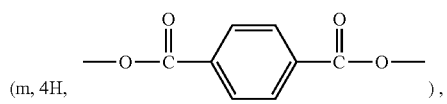

), 6.7-6.9 (m, 4H,

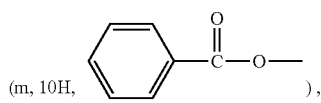

4.32 (m, 2H, COOC$\underline{H}_2$CH$_2$O), 3.83 (m, 2H, COOCH$_2$C$\underline{H}_2$O), 3.42 (s, 24H, OC$\underline{H}_3$), 2.1 (m, 6H, COC$\underline{H}_3$).

Characteristic peak positions in infrared spectroscopy: ester carbonyl, 1730-1740 cm$^{-1}$; C—O—C in ester group, 1200 cm$^{-1}$; characteristic absorption peak of P=N bond in the skeleton of phosphazene, 1217 cm$^{-1}$; P—N in the skeleton of phosphazene, 874 cm$^{-1}$; absorption peak of methyl ether, 2995.3 cm$^{-1}$; absorption peak of P—O—C bond, 1035 cm$^{-1}$; absorption peak of CH$_2$—O, 2983 cm$^{-1}$; para-position substituted benzene ring, 860-790 cm$^{-1}$.

128 g of the above ester compound C as a curing agent was added into 100 g of o-cresol novolac epoxy resin with an epoxide equivalent of 1200 g/eq and 0.2 g of curing accelerator 2MI to prepare an epoxy resin composition. A standard copper clad laminate sample meeting the national, UL and other standards was prepared by using this epoxy resin composition according to generally used copper clad laminate production process. The copper clad laminate is named as copper clad laminate c and the properties thereof are measured and the results are shown in Table 1.

Example 4

The phosphazene compound of the present example has the following structure:

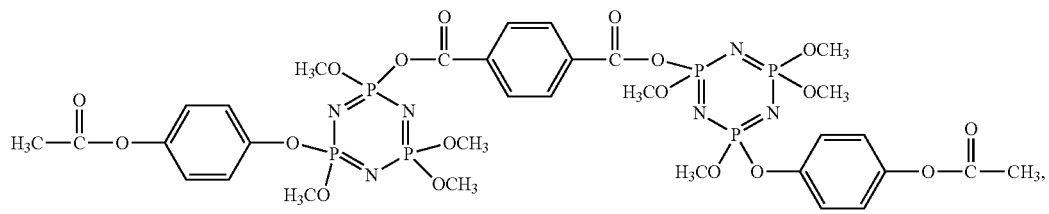 [SMILES: COP1(OC)=NP(OC)(OC(=O)c2ccc(C(=O)OP3(OC)=NP(OC)(Oc4ccc(OC(C)=O)cc4)=NP(OC)(OC)=N3)cc2)=NP(OC)(Oc2ccc(OC(C)=O)cc2)=N1]

and the preparation method thereof is shown as follows.

1 mol of hydroquinone, 1 mol of acetic acid, 200 ml of acetone were added to a 3-neck glass reactor having a volume of 2000 ml and having a stirring apparatus. 3 mL of 98% concentrated sulfuric acid was dripped therein and the mixture conducted esterification reaction for 1 h, followed by adding 1 mol of hexachlorocyclotriphosphazene and 4 mol of sodium methylate and stirring. While stirring, nitrogen was fed therein, and the reactor was heated to 60° C. 621 g of 20% sodium hydroxide solution was dripped within 60 min, and then the mixture was held at 60° C., stirred and reacted for 10 hours. After reaction, the inorganic constituents and water in the system were removed by physical methods. Then 3 mL of 98% concentrated sulfuric acid was dripped and 1 mol of terephthalic acid was added therein, and the mixture was continued to be held at 60° C. and react for 3 hours, followed by adding 1 mol of hexachlorocyclotriphosphazene and continuing to react for 5 hours, and then adding 4 mol of sodium methylate and 1 mol of hydroquinone and continuing to react for 8 hours. After reaction, the inorganic constituents and water in the system were removed by physical methods. Then 3 mL of 98% concentrated sulfuric acid was dripped and 1 mol of acetic acid was added therein, and the mixture reacted for 2 hours. After reaction, the impurities and water in the system were removed by physical methods; and the solvent in the system was distilled off to obtain 1 mol of ester compound D having an ester equivalent of 250 g/eq and a structure as shown above.

The obtained compound D was characterized by nuclear magnetic resonance hydrogen spectrum, and the results are as follows:

$^1$H NMR (CDCl$_3$, 500 MHz): δ 8.28-8.32 (m, 4H, (m, 4H, 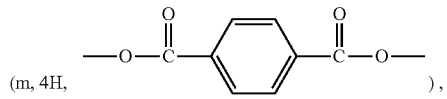 ), 6.7-6.9 (m, 8H, (m, 10H, 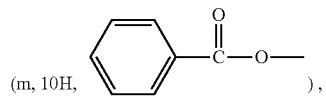 ), 3.42 (s, 24H, OC$\underline{H}_3$), 2.1 (m, 6H, COC$\underline{H}_3$).

Characteristic peak positions in infrared spectroscopy: ester carbonyl, 1730-1740 cm$^{-1}$; C—O—C in ester group, 1200 cm$^{-1}$; characteristic absorption peak of P=N bond in the skeleton of phosphazene, 1217 cm$^{-1}$; P—N in the skeleton of phosphazene, 874 cm$^{-1}$; absorption peak of methyl ether, 2995.3 cm$^{-1}$; absorption peak of P—O—C bond, 1035 cm$^{-1}$; absorption peak of CH$_2$—O, 2983 cm$^{-1}$; para-position substituted benzene ring, 860-790 cm$^{-1}$.

125 g of the above ester compound D as a curing agent was added into 100 g of o-cresol novolac epoxy resin with an epoxide equivalent of 200 g/eq and 0.2 g of curing accelerator 2MI to prepare an epoxy resin composition. A standard copper clad laminate sample meeting the national, UL and other standards was prepared by using this epoxy resin composition according to generally used copper clad laminate production process. The copper clad laminate is named as copper clad laminate d and the properties thereof are measured and the results are shown in Table 1.

Comparative Example 1

200 g of o-cresol novolac epoxy resin with an epoxide equivalent of 200 g/eq was added into 105 g of linear phenolic resin curing agent with a phenolic hydroxyl equivalent of 105 g/eq and 70 g of hexaphenoxyphosphazene which is used as flame retardant and 0.2 g of 2-methylimidazole, and the mixture was dissolved in a suitable amount of butanone to form a solution. A copper clad laminate e having a resin content of 50% was prepared by using standard glass fiber cloth according to a well-known method. The properties of the copper clad laminate e are shown in Table 1.

Comparative Example 2

200 g of o-cresol novolac epoxy resin with an epoxide equivalent of 200 g/eq was added into 220 g of a resin compound having a structure of Formula (I) and an ester equivalent of 220 g/eq and 70 g of hexaphenoxyphosphazene which is used as flame retardant and 0.2 g of pyridine, and the mixture was dissolved in a suitable amount of butanone to form a solution. A copper clad laminate f having a resin content of 50% was prepared by using standard glass fiber cloth according to a well-known method. The properties of the copper clad laminate f are shown in Table 1.

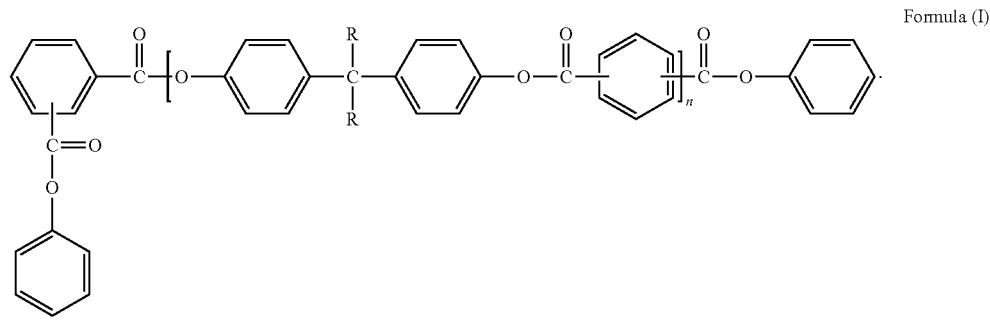

Formula (I)

The test results of products of Examples and Comparative Examples are shown in Table 1 (the specific test methods are not described considering that they are well-known by those skilled in the art).

TABLE 1

| Test Item | Copper clad laminate a | Copper clad laminate b | Copper clad laminate c | Copper clad laminate d | Copper clad laminate e | Copper clad laminate f |
| --- | --- | --- | --- | --- | --- | --- |
| Tg (DSC) (° C.) | 183 | 180 | 175 | 178 | 150 | 135 |
| T-peeling strength (kg/mm$^2$) | 1.93 | 2.03 | 2.01 | 1.90 | 1.71 | 1.69 |
| Interlaminar peeling strength (kg/mm$^2$) | 1.64 | 1.65 | 1.75 | 1.73 | 0.80 | 0.82 |
| Saturated water absorption (%) | 0.34 | 0.32 | 0.33 | 0.35 | 0.58 | 0.60 |
| Dielectric constant (1 GHz) | 3.32 | 3.25 | 3.30 | 3.27 | 4.25 | 4.3 |
| Dielectric loss (1 GHz) | 0.0056 | 0.005 | 0.006 | 0.0058 | 0.13 | 0.14 |

As can be seen from Table 1, the copper clad laminates of the present invention prepared by using an epoxy resin composition prepared by using a compound having a structure of Formula (I) as a curing agent have a dielectric constant (1 GHz) of 3.28-3.33, a dielectric loss (1 GHz) of 0.005-0.006, a Tg which can be 175° C. or greater, a T-peeling strength which can be 1.90 kg/mm$^2$ or greater, an interlaminar peeling strength which can be 1.64 kg/mm$^2$ or greater, and a saturated water absorption which can be 0.35% or less, which are much better than the properties of the copper clad laminates of Comparative Examples.

The present invention illustrates the phosphazene compound, prepreg and composite metal laminate of the present invention by the above examples, but the present invention is not limited to the above examples; that is to say, it does not mean that the present invention must be conducted by relying on the above examples. Those skilled in the art should understand that any modification to the present invention, any equivalent replacement of each raw material of the products of the present invention and the addition of auxiliary ingredients, the selection of specific embodiment and the like all fall into the protection scope and the disclosure scope of the present invention.

The invention claimed is:

1. A phosphazene compound, comprising a molecular structure as shown in Formula I:

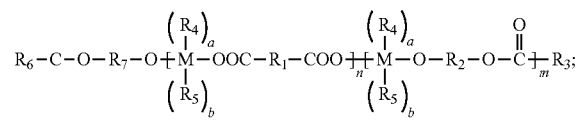

Formula (I)

in Formula I, $R_1$ is substituted or unsubstituted aromatic hydrocarbon group or substituted or unsubstituted aliphatic hydrocarbon group; $R_2$, $R_3$, $R_6$ and $R_7$ are independently any organic group satisfying the chemical environment thereof; $R_4$ and $R_5$ are independently any inert nucleophilic group; M is any one of cyclotriphosphazene groups $M_1$, cyclic ring consisting of four or more phosphazene groups $M_2$, or non-cyclic polyphosphazene groups $M_3$, or a combination of at least two of them; n is an integer greater than or equal to 1 and m is an integer greater than or equal to zero; each a and b is an integer greater than or equal to zero, and a+b+2 equals to two times of the number of phosphorus atoms in M group.

2. The phosphazene compound of claim 1, wherein $R_1$ is any one of substituted or unsubstituted straight-chain alkylene, substituted or unsubstituted branched alkylene, substituted or unsubstituted cycloalkylene, substituted or unsubstituted arylene, substituted or unsubstituted heteroarylene, substituted or unsubstituted arylenealkylene, substituted or unsubstituted alkylenearylene, substituted or unsubstituted cycloalkylenearylene, substituted or unsubstituted heteroarylenealkylene or substituted or unsubstituted alkyleneheteroarylene.

3. The phosphazene compound of claim 1, wherein $R_2$ and $R_7$ are independently any one substituted or unsubstituted straight-chain alkylene, substituted or unsubstituted branched alkylene, substituted or unsubstituted cycloalkylene, substituted or unsubstituted arylene, substituted or unsubstituted heteroarylene, substituted or unsubstituted arylenealkylene, substituted or unsubstituted alkylenearylene, substituted or unsubstituted cycloalkylenearylene, substituted or unsubstituted heteroarylenealkylene, or substituted or unsubstituted alkyleneheteroarylene.

4. The phosphazene compound of claim 1, wherein $R_3$ and $R_6$ are independently any one of substituted or unsubstituted straight-chain or branched alkyl, substituted or unsubstituted cycloalkyl, substituted or unsubstituted aryl, substituted or unsubstituted heteroaryl, substituted or unsubstituted aralkyl, substituted or unsubstituted heteroarylalkyl.

5. The phosphazene compound of claim 1, wherein $R_4$ and $R_5$ are independently any one of substituted or unsubstituted alkoxy, substituted or unsubstituted cycloalkoxy, substituted or unsubstituted aryloxy, substituted or unsubstituted arylalkoxy, substituted or unsubstituted alkylaryloxy, substituted or unsubstituted heteroarylalkoxy, substituted or unsubstituted alkylheteroaryloxy, substituted or unsubstituted carboxylate group, substituted or unsubstituted carbonate group, substituted or unsubstituted sulfonate group, substituted or unsubstituted phosphonate group, or a combination of at least two of them.

6. The phosphazene compound of claim 1, wherein $M_1$ has a structure of

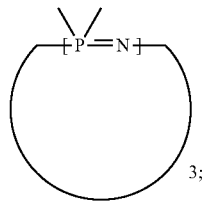

$M_2$ has a structure of

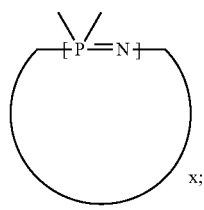

wherein x is greater than or equal to 4;

$M_3$ has a structure of

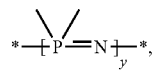

wherein y is greater than or equal to 3.

7. A method for preparing the phosphazene compound of claim 1, obtaining the phosphazene compound by carrying out a nucleophilic substitution reaction of phosphazene chloride and nucleophile.

8. A prepreg prepared by impregnating a substrate with an epoxy resin composition comprising the phosphazene compound of claim 1 or coating an epoxy resin composition comprising the phosphazene compound of claim 1 onto a substrate.

9. The prepreg of claim 8, wherein the substrate is a glass fiber substrate, a polyester substrate, a polyimide substrate, a ceramic substrate or a carbon fiber substrate.

* * * * *